United States Patent [19]
Katakura

[11] 3,953,823
[45] Apr. 27, 1976

[54] VELOCITY MEASUREMENT APPARATUS USING PULSED ULTRASONIC WAVES

[75] Inventor: Kageyoshi Katakura, Tokyo, Japan

[73] Assignee: Hitachi Medical Corporation, Japan

[22] Filed: Mar. 31, 1975

[21] Appl. No.: 563,396

[30] Foreign Application Priority Data
Mar. 29, 1974  Japan.............................. 49-35745

[52] U.S. Cl................................ 340/1 R; 340/3 D; 128/2.05 F; 324/160
[51] Int. Cl.².......................................... G01S 9/68
[58] Field of Search.......... 324/160, 166, 178, 79 R, 324/79 D; 340/1 R, 3 DI; 343/13, 8, 9; 128/2 V, 2.05 F

[56] References Cited
UNITED STATES PATENTS

| | | | |
|---|---|---|---|
| 2,987,701 | 6/1961 | Grannemann | 340/15 |
| 3,474,444 | 10/1969 | Okamoto | 343/7 |
| 3,498,290 | 3/1970 | Shaw et al. | 128/2.05 |
| 3,696,324 | 10/1972 | Baum | 340/1 R |
| 3,728,026 | 4/1973 | Idestrom et al. | 356/5 |
| 3,733,581 | 5/1973 | Kalmus | 340/1 R |
| 3,896,788 | 7/1975 | Sato | 128/2.05 F |

Primary Examiner—R. V. Rolinec
Assistant Examiner—Vincent J. Sunderdick
Attorney, Agent, or Firm—Craig & Antonelli

[57] ABSTRACT

A velocity measurement apparatus using pulsed ultrasonic waves which includes a transmitting section which projects pulsed ultrasonic waves to a target at a predetermined position and a receiving section which detects echoes from the target and the Doppler shift. The transmitting section, in order to remove undesirable echoes, causes the polarity of the ultrasonic pulse to be changed at random and the receiving section removes the undesirable echoes by using the irregular polarity of the pulsed ultrasonic echoes.

17 Claims, 9 Drawing Figures

VELOCITY MEASUREMENT APPARATUS USING PULSED ULTRASONIC WAVES

BACKGROUND OF THE INVENTION

1. Field of the Invention

This invention relates to velocity measurement apparatus, more particularly to an apparatus for measuring the velocity of a moving target by using the Doppler shift of pulsed ultrasonic waves.

2. Description of the Prior Art

Velocity measurement apparatus using the Doppler shift of ultrasonic pulsed waves are known. For example, such an apparatus, is used for measuring the velocity of blood-flow. This type of velocity measurement apparatus basically comprises a transmitting transducer which projects ultrasonic pulsed waves to a moving target, a receiving transducer for detecting echoes from the target, a phase detector or comparator for sensing the Doppler shift due to the velocity of the target, and a device which transforms the output of the phase detector into velocity information.

In order to operate this type of apparatus effectively, the following relationships must exist:

$$\Delta f \leq 1/(2T)$$

$$d = (CT)/2$$

where $\Delta f$ is the Doppler shift frequency, $T$ is the pulse repetition pitch or interval, $C$ is the velocity of sound in the medium in question, and $d$ is the distance between the transducers and the target.

Since the Doppler shift frequency $\Delta f$ is proportional to the velocity of the moving target, it appears that the maximum detectable velocity of the target is small if the distance involved is large. This fact poses a serious problem for uses of the apparatus for blood flow velocity measurement as it becomes virtually impossible to measure the velocity of high speed blood flow deep within the body.

SUMMARY OF THE INVENTION

An object of the present invention is to improve conventional velocity measurement apparatus using pulsed ultrasonic waves.

Another object of the present invention is to provide a velocity measurement apparatus for detecting blood flow independently of the depth or position in the body.

A further object of the present invention is to prove a velocity measurement apparatus in which the influence of undesirable echoes is eliminated.

In order to achieve the above mentioned objects, the present invention provides a velocity measurement apparatus incorporating the features that the transmitting section is constructed so that the polarity of the pulsed ultrasonic waves projected from the transmitting transducer are changed or modulated irregularly and the receiving section is constructed so that only the echoes from the target to be measured and from those targets having a predetermined distance or positional relationship with the target to be measured are compared with a reference signal by a phase comparator. Undesirable outputs from the phase comparator corresponding to targets not to be measured are removed or eliminated by utilizing the irregular polarity of the waves.

According to the present invention, the transmitting section of the velocity measurement apparatus includes:

a. a pulse modulated sine wave signal source;
b. a circuit for irregularly inverting the polarity of the pulse modulated sine wave signal; and
c. a transmitting transducer for transducing the output of the circuit into an acoustic signal, that is, pulsed ultrasonic waves and projecting those pulsed ultrasonic waves toward a target; and the receiving section includes:
d. a receiving transducer for sensing the echoes from the targets and converting such echoes into electrical signals;
e. a first device for detecting only those parts of the electric signal from the target to be measured;
f. a phase comparator for comparing the output of the first device with a reference pulse modulated sine wave signal;
g. a second device for changing the polarity of either one of the outputs of the first device or the reference pulse modulated signal so as to equalize the polarities of both signals; and
h. a frequency analyzer for detecting a Doppler shift signal from the output of the phase comparator.

These and other objects, features and advantages of the present invention will become more apparent from the following description when taken in connection with the accompanying drawings which show, for purposes of illustration several embodiments in accordance with the present invention.

DESCRIPTION OF THE PREFERRED EMBODIMENTS

Figure 1:
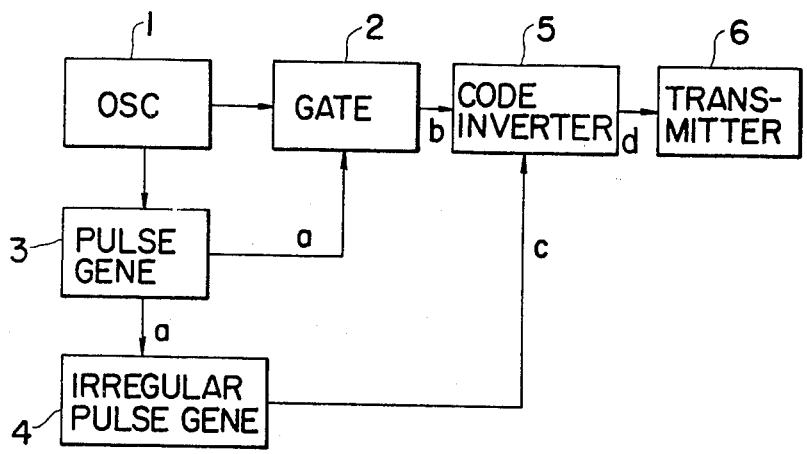
FIG. 1 is a block diagram of an embodiment of a transmission section of the velocity measurement apparatus in accordance with the present invention.

Referring now to the drawings wherein like reference numerals designate like parts throughout the several views, there is illustrated in FIG. 1 a block diagram of an embodiment of a transmitting section of a velocity measurement apparatus in accordance with the present invention. In FIG. 1, a signal generator or master oscillator 1 produces a continuous sine wave signal the frequency of which is normally about 2~5 MHz. One part of the signal from the master oscillator 1 is supplied to a pulse generator 3 which includes a ripple counter for dividing the master oscillator frequency down to a pulse repetition frequency and digital logic circuits with the pulse generator generating a pulse train as shown in (a) of FIG. 2. This pulse train is synchronized with the sine wave signal from the master oscillator. The width $t$ of a pulse in the pulse train is approximately 4 $\mu$s. The sine wave signal from the oscillator 1 and one part of the pulse train (a) from the generator 3 are supplied to a range gate circuit 2 comprising, for example, diodes. The gate circuit 2 produces a pulsed sine wave train as shown in (b) in FIG. 2. For the sake of simplicity, each pulsed sine wave is shown as only one wave length, but in practice, there are several sine waves equal to the wave number of the interval $t$ of each pulse.

Figure 2:
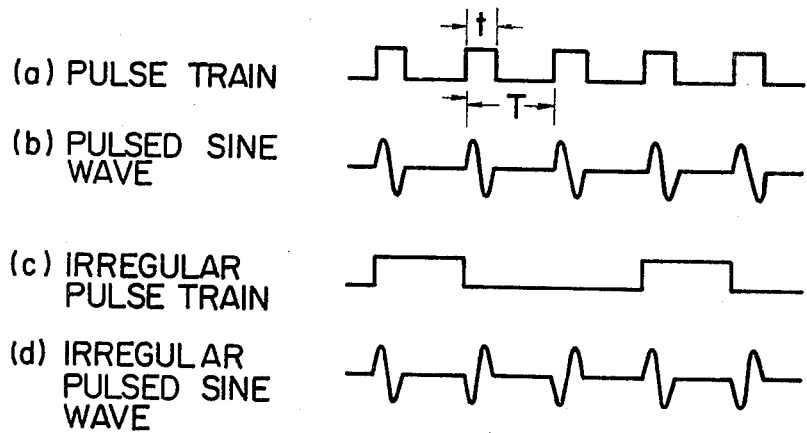
FIG. 2 illustrates time and wave form charts explaining the operation of FIG. 1.

The other part of the pulse train (a) from the pulse generator 3 is supplied to an irregular signal generator 4 which produces a pulse train (c) as shown in FIG. 2. In this pulse train, each elemental pulse is produced at an irregular interval such as in accordance with an M sequence code and the time points of the rise and fall of each irregular elemental pulse are synchronized with the pulses of the pulse train (a).

The irregular pulse train (c) and the pulsed sine wave (b) are supplied to a code inverter 5 which may be, for example, a balanced modulator which produces another pulsed sine wave train (d) as shown in FIG. 2. The polarities of this pulsed sine wave train (d) are reversed at irregular intervals according to the polarities of the irregular pulse train (c). The output (d) of the code inverter 5 which is electrical is supplied to an electro-acoustic transducer 6 comprising for example PZT (Lead-Zirconate-Titanate) for conversion to an acoustic form and is projected to the target to be measured as a pulsed ultrasonic wave.

Figure 3A:
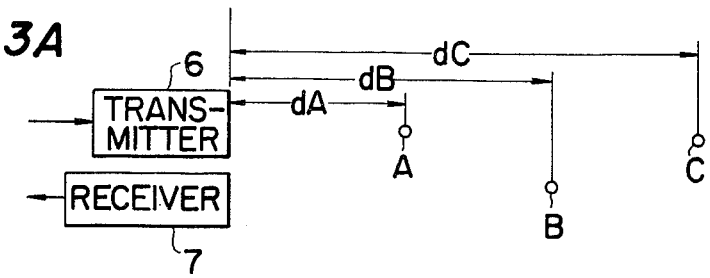
FIG. 3A shows the positional relationship between the transducers and targets.
Figure 3B:
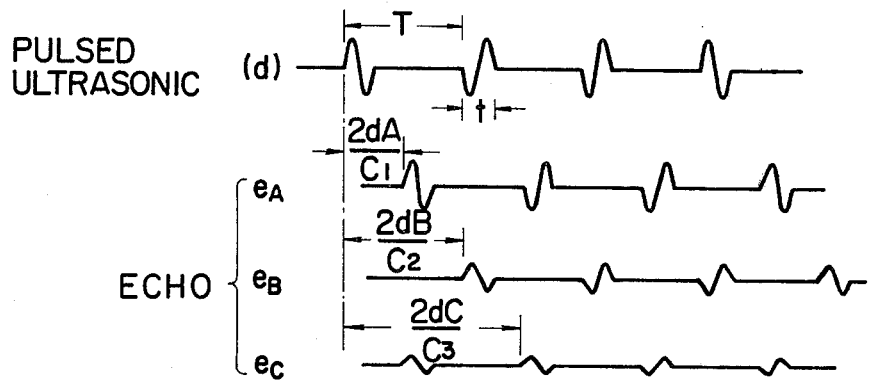
FIG. 3B is a time chart showing the output of the transducer.

FIGS. 3A and 3B show the positional relationship between transmitting and receiving transducers 6 and 7 and a plurality of stationary targets as well as the received signals or returned echoes. As shown in FIG. 3A the transmitting transducer 6 and the receiving transducer 7 are located at the same position, and the three reflective targets A,B and C are positioned apart from the transducers by distances $dA$, $dB$ and $dC$, respectively. FIG. 3B shows the time relationships between a pulsed ultrasonic wave (d) projected from the transmitting transducer 6 and the three echoes which are reflected by the three targets A,B and C. Although the three echoes $e_A, e_B, e_C$ are shown separately for the sake of clarification, they are in fact, superposed. As can be seen from FIGS. 3A and 3B, the three echoes $e_A, e_B$, and $e_C$ have delay times which correspond to the round trip transmission times $$\frac{2dA}{C1}, \frac{2dB}{C1}, \text{ and } \frac{2dC}{C1}$$

respectively, where C1 is the velocity of an ultrasonic wave in the medium in question.

Figure 4:
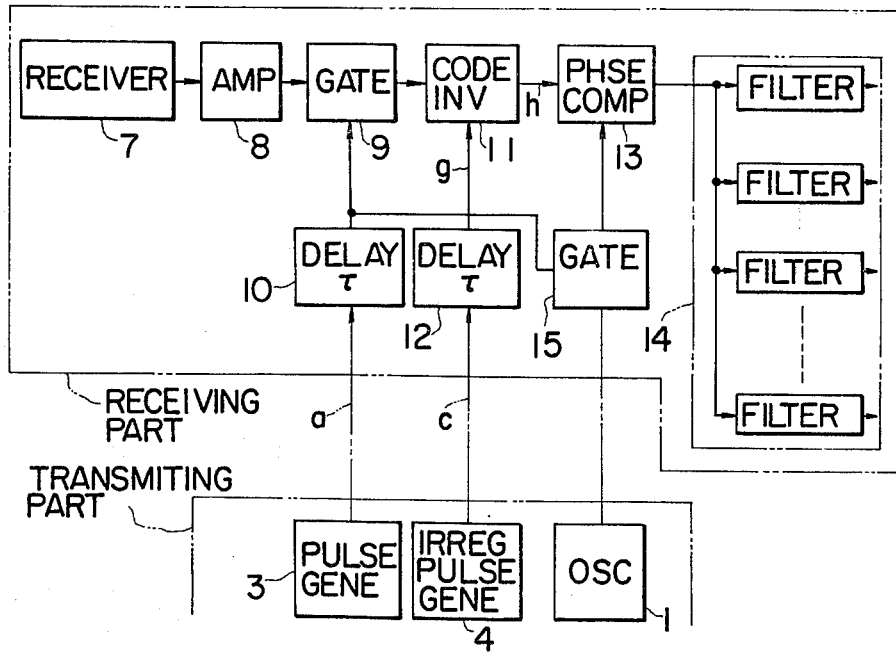
FIG. 4 is a block diagram illustrating an embodiment of a receiving section of the velocity measurement apparatus in accordance with the present invention.

FIG. 4 is a block diagram illustration of a receiving section of the velocity measurement apparatus in accordance with an embodiment of the present invention. Echoes such as $e_A$, $e_B$ and $e_C$ are detected and transformed into electrical signals by the receiving transducer 7 which corresponds to the transducer 7 in FIG. 3A. The output signal of the transducer 7 is amplified by an amplifier 8, and supplied to a gate circuit 9, which has a construction similar to that of the gate circuit 2 in FIG. 1.

In order to drive the gate circuit 9, the pulse train (a) from the pulse generator 3 is supplied to the gate circuit 9 through a delay circuit 10 having a predetermined delay time $\tau$ corresponding to the round trip transmission time to the target to be measured.

The output of the gate circuit 9 is supplied to a code inverter 11 which is constructed similarly to the inverter 5 in FIG. 1, e.g. a balanced modulator. Additionally, the irregular pulse train (c) from the irregular pulse generator 4, in the transmitting portion is supplied to the code inverter 11 through delay circuit 12 having the same delay time $\tau$ and the same construction as the delay circuit 10.

The output signal (h) of the code inverter 11 is supplied to a phase comparator 13 and compared with a pulsed sine wave resulting from the output of the master oscillator 1 in the transmitting portion fed through a gate circuit 15 gated in accordance with the output of the delay circuit 10. The output of the phase comparator 13 is fed to a frequency analyzer 14 which is, for example, formed of a plurality of band pass filters each of which has a different center frequency and which are connected in parallel with each other. By measuring the output of the frequency analyzer, the velocity of the target to be measured can be determined in a conventional manner.

Figure 5:
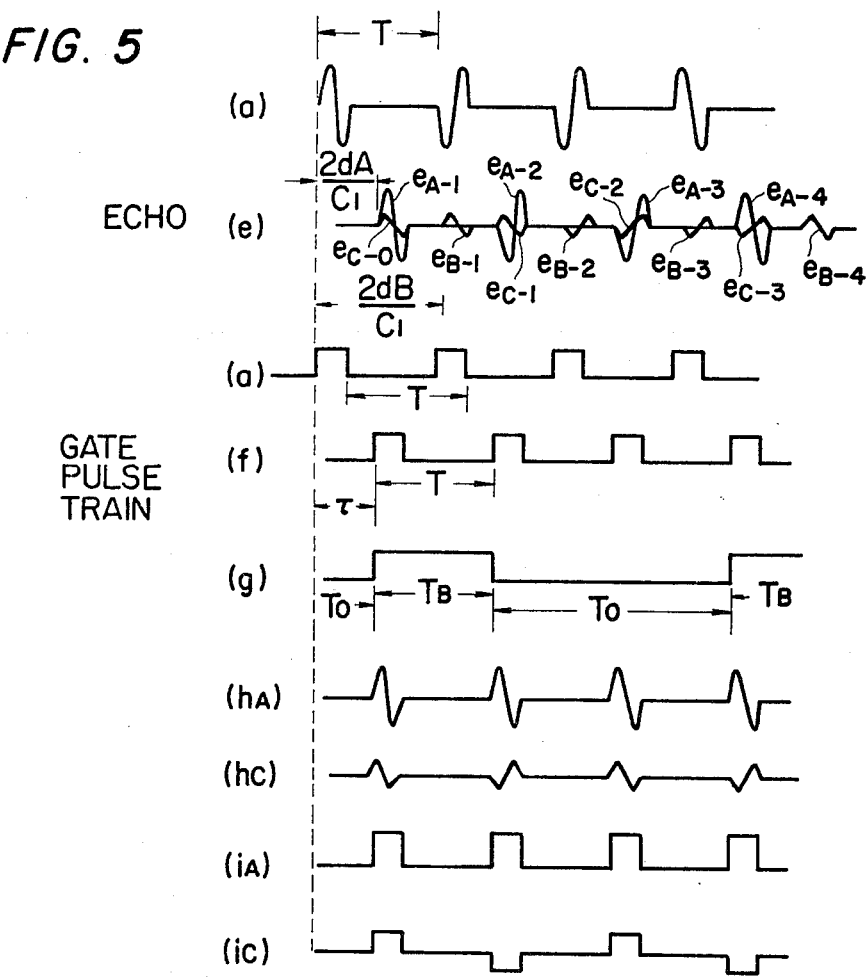
FIG. 5 illustrates time and wave-form charts for explaining the operation of FIG. 4.

The operation and the advantages of the present invention will become apparent from the following description in connection with FIG. 5. First of all, the explanation will be directed to the reason that the velocity measurement apparatus according to the present invention can detect the velocity of a specified target to be measured in spite of the fact that a plurality of targets are located at different positions as shown by A,B and C in FIG. 3A. For sake of clarity, the explanation relates to the case wherein all targets are stationary or at a predetermined position. However, the present invention is also applicable to moving targets.

Assuming that three targets A,B and C are arranged as shown in FIG. 3A and that the distance $dC$ is twice the distance $dA$, and that the target A is the specified target to be measured, then the output signal of the receiving transducer 7 or the amplifier 8 is as shown in (e) in FIG. 5. This output signal corresponds to the echo signals $e_A$, $e_B$, and $e_C$ superposed on the same time scale and is range gated by a gate pulse train (f) in the gate circuit 9. As described above, this gate pulse train (f) is produced by the output of the pulse generator 3, i.e. the pulse train (a) and delayed by the time $$\tau = \frac{2dA1}{C1}.$$

Therefore, only the echo components $e_A$ and $e_C$ which are synchronized with the gate pulse train can pass through the gate circuit 9, and the echo $e_B$ which is not synchronized with the gate pulse train (f) is eliminated.

However, as described above, there is still an undesirable echo component $e_C$ which is backscattered from target C in the output stage of gate circuit 9. This undesirable echo component $e_C$ is removed as follows. The output of the gate circuit 9 is supplied to the code converter 11 which converts the polarity of the input signal in such a manner that the polarity of the input pulsed sine wave is reversed during the pulse time $\tau$ from the delay circuit 12. Accordingly, the polarity of the outputs corresponding to the echoes of the components $e_{A-2}$, $e_{A-3}$, $e_{C-1}$ and $e_{C-2}$ from the code inverter 11 are reversed. The output signals corresponding to the echoes $e_A$ and $e_C$ are shown in FIg. 5 as $hA$ and $hC$, respectively. They are shown separately for the sake of clarity, but in practice, they are superposed on the same time scale. It can be seen that each phase of the pulsed sine wave $hA$ is the same, but that of the pulsed sine wave $hC$ is changed irregularly.

When these signals $hA$ and $hC$ are compared with the standard or reference pulsed sine wave signal from the oscillator 1 the signals $hA$ and $hC$ are converted into pulse trains $iA$ and $iC$ as shown in FIG. 5. The amplitudes of these pulse trains $iA$ and $iC$ are proportional to the signal amplitudes of $hA$ and $hC$ and to the phase difference between the output signals $h$ and the standard sine wave. The mean value of the pulse train $hA$ during a fixed time interval has a certain value, but that of the pulse train $hC$ becomes zero. This means that the output corresponding to the undesirable echo component $e_C$ is removed.

In the above description, the explanation has been directed to the case wherein targets A, B and C are stationary in order to explain simply the manner in which the influence of undesirable echoes can be eliminated. In practice, these stationary echoes are removed by a digital notch filter, the same as in the MTI processor. In the case that the targets or reflective objects are moving, the frequency of the echoes is changed in proportion to the velocity of the target. Accordingly, a phase difference appears between the standard sine wave signal from the master oscillator 1 and the output signal corresponding to the echo due to the target A to be measured. This is shown as $jA$ in FIG. 6. This pulse train corresponds to $iA$ in FIG. 5. The dotted envelope line K in FIG. 6 is a sine wave the frequency $\Delta f$ of which depends on the velocity of the moving target A, that is, on the Doppler shift.

It is well known that the following relationship exists between a frequency $f$ of a standard sine signal. The Doppler shift $\Delta f$, a radial velocity v of a moving target A and the velocity $C_1$ of sound in the medium $$v = \frac{\Delta f c1}{2f}$$

As the values of $c1$ and $f$ are predetermined, the velocity $v$ of moving target A can be determined if the value of $\Delta f$ is first determined.

Figure 6:
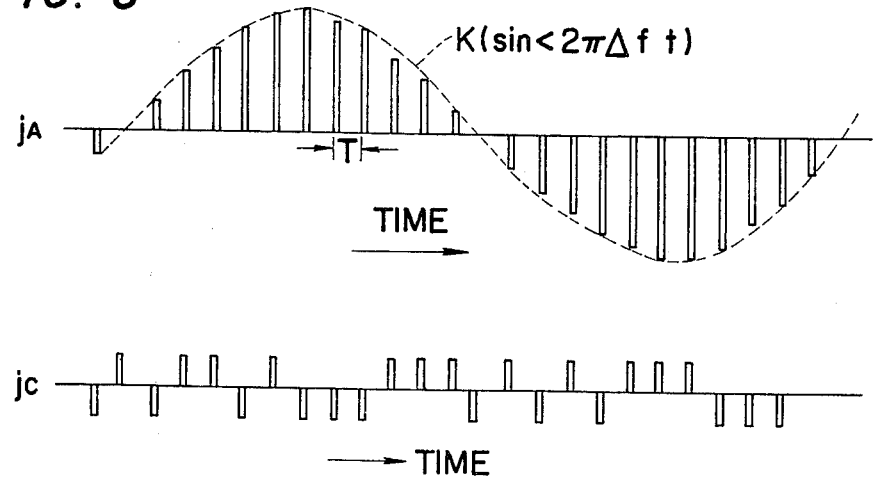
FIG. 6 illustrates the wave forms of the output signal from the phase comparator of the receiving section.

In accordance with the present invention, the polarity of the output signal or pulse train $iC$ corresponding to the undesirable echo due to target C as in FIG. 5 is shown by the irregular waveform $jC$ in FIG. 6 whether target C is moving or not. For this reason, when the output signal of the phase comparator 13 is filtered and smoothed by the frequency analyzer formed of a plurality of band pass filters, only those components having a frequency $\Delta f$ are detected and the component which correspond to the pulse train $iC$ or $jC$ do not appear at the output terminals of the filters because they do not have a fixed frequency component. Accordingly, the velocity of the target A can be determined by utilizing a computer to calculate the outputs of the filters or by displaying the outputs on a cathode ray tube.

Figure 7:
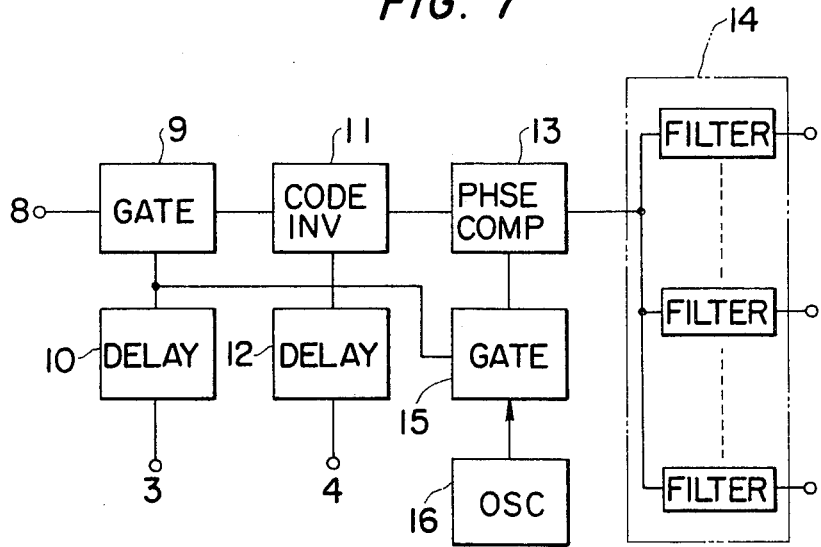
FIG. 7 is a block diagram of a portion of a receiving section in accordance with another embodiment of the present invention.

FIG. 7 illustrates a portion of a receiver section in accordance with another embodiment of the velocity measurement apparatus of the present invention. In this embodiment, the construction and operation of all the blocks except the reference signal oscillator 16 are basically the same as that of the similar numbered blocks in FIG. 4, such that the description of these blocks will be omitted.

Although the reference signal of the embodiment shown in FIG. 4 depends on the oscillator 1, the frequency of the reference signal is approximately the same as that of the output sine wave signal of the oscillator 1. Accordingly, it is impossible to detect the direction of movement of the targer that is, whether the target is approaching or moving away. However, the reference signal of the embodiment of FIG. 7 is independent of the oscillator, and the frquency thereof is slightly higher than that of the oscillator 1 by a fixed frequency $F_1$, for example, about 5 KHz.

Assuming a Doppler shift frequency of $\Delta f$, then the frequency of the output of the frequency analyzer is detected as $F \pm \Delta f$. The plus or minus code ($\pm$) indicates the moving direction of the target to be measured. Therefore, it is possible to measure the velocity of the target by detecting the frequency shift $\Delta f$ from the frequency F and to measure the direction of movement of the target by detecting whether the frequency of the frequency analyzer is higher or lower than the fixed frequency F.

Figure 8:
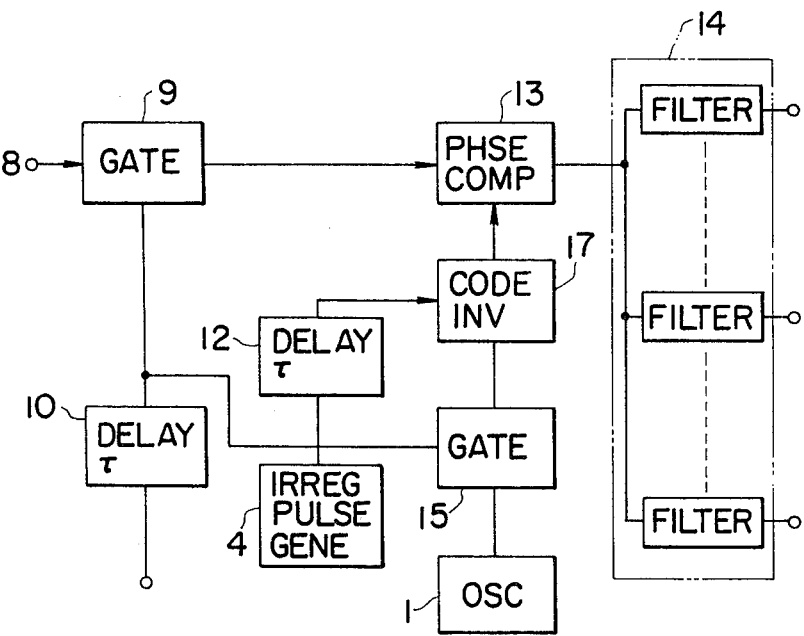
FIG. 8 is a block diagram of a portion of a receiving section in accordance with another embodiment of the present invention.

FIG. 8 shows another embodiment of a portion of the velocity measurement apparatus according to the present invention. In this embodiment, the output of the gate circuit 9 is supplied directly to the phase comparator 13, and the reference signal is formed by gating the output signal of the gate circuit 15 and by, thereafter, code inverting the output of the gate circuit in the code inverter 17. The construction and operation of the gate circuit 15 and the code inverter 17 are basically the same as those of the gate circuit 15 and the code inverter 11 except for the fact that the input signal comes from the oscillator 1. This embodiment has the advantages that the operation of code inversion is carried correctly and that the construction of the code inverter is simplified since the input signal from the oscillator is not distorted.

The velocity measurement apparatus according to the present invention is useful in various fields of velocity measurements and especially in blood flow measurement. Blood vessels are distributed at various depths in the body and the maximum measurable blood velocity is closely related to the distance between the blood vessel and the transmitting and receiving transducers of conventional pulsed ultrasonic wave pulsed flow measurement apparatus. However, a velocity measurement apparatus can easily measure the maximum blood flow velocity in the body independently of the depth of the blood vessel because of the reasons described above.

While I have shown and described several embodiments in accordance with the present invention, it is understood that the same is not limited thereto but is susceptible of numerous changes and modifications as known to a person skilled in the art and I therefore do not wish to be limited to the details shown and described herein but intend to cover all such changes and modifications as are obvious to one of ordinary skill in the art.

For example, for the sake of clarity, the above embodiments have been directed to an apparatus for measuring the velocity of one target located at a fixed position. However, this apparatus according to the present invention can also be utilized for measuring the velocities of a plurality of reflecting targets at the same time by constructing parallel receiving sections corresponding to different time delays. Also, the frequency analyzer can be substituted for a conventional analyzer and smoothing device such as a digital Fourier converter or a time compressed heterodyne frequency analyzer.

I claim:

1. Velocity measurement apparatus comprising:
   transmitting means for projecting a pulsed ultrasonic wave toward at least one target, said transmitting means including generating means for generating a pulse modulated signal having an irregularly changing polarity, and transmitting transducer means for converting the output of the generating means into a pulsed ultrasonic wave and for projecting the pulsed ultrasonic wave toward the target to be measured; and
   at least one receiving means for receiving echoes reflected from the target, said receiving means including receiving transducer means for converting the received echoes into an electrical signal, first means for deriving a signal of the echo components which are delayed by the transmission time between the target to be measured and the transmitting and receiving transducer means, second means for generating a reference pulse modulated signal in synchronization with the output of said generating means, third means for inverting the polarity of one of the output of the first means and of the second means in correspondence with the irregularity in the polarity of the signal provided by said generating means, phase comparator means for comparing the output of said third means with one of the output of said first and said second means, and frequency analyzer means for determining the Doppler shift in response to the output of said phase comparator means.

2. Velocity measurement apparatus according to claim 1, wherein said generating means generates a pulse modulated sine wave signal and said second means generates a reference pulse modulated sine wave signal.

3. Velocity measurement apparatus according to claim 2, wherein said generating means includes first oscillator means for providing a continuous sine wave output signal, pulse signal generator means responsive to the output of said first oscillator means for providing a pulsed signal having a predetermined repetition frequency, irregular pulse generator means for generating an irregular pulse signal in synchronism with the output of said pulse generator means, first gate circuit means responsive to the pulse signal from said pulse signal generator means for converting the output signal from said oscillator means into a pulse modulated signal wave signal, and first code inverter means responsive to the output of said irregular pulse generator means for inverting the polarity of the pulse modulated sine wave signal from said first gate circuit means in accordance with the irregular pulse signal from said irregular pulse generator means.

4. Velocity measurement apparatus according to claim 3, wherein said first means for deriving a signal of the echo components includes second gate circuit means for receiving the output of said receiving transducer means, and first delay circuit means having a delay time equal to the transmission time between the target to be measured and the transmitting and receiving transducer means, said first delay circuit means receiving a pulse signal from said pulse signal generator means and for providing a delayed pulse signal to said second gate circuit means.

5. Velocity measurement apparatus according to claim 4, wherein said second means includes third gate circuit means responsive to the output from said first delay circuit means for gating a continuous sine wave signal which is in synchronism with the output of said generating means so as to provide a reference pulse modulated sine wave signal.

6. Velocity measurement apparatus according to claim 5, wherein said third means includes second code inverting means for inverting the polarity of the output of said second gate circuit means, and second delay circuit means having a delay time equal to that of said first delay circuit means for delaying the output of said irregular pulse generator means and providing a delayed irregular pulse signal to said second code inverter means.

7. Velocity measurement apparatus according to claim 5, wherein said third means includes second code inverting means for inverting the polarity of the output of said third gate circuit means, and second delay circuit means having a delay time equal to the delay time of said first delay circuit means for delaying the output of said irregular pulse generator means and providing a delayed irregular pulse signal to said second code inverter means.

8. Velocity measurement apparatus according to claim 5, wherein said third gate circuit means receives the output of said first oscillator means as the continuous sine wave input signal thereof.

9. Velocity measurement apparatus according to claim 5, wherein said second means further includes second oscillator means for providing a continuous sine wave signal to said third gate circuit means.

10. Velocity measurement apparatus according to claim 9, wherein said second oscillator means has a frequency which is higher than said first oscillator means.

11. Velocity measurement apparatus according to claim 2, wherein frequency analyzer means includes a plurality of band pass filter means.

12. Velocity measurement apparatus according to claim 6, wherein said third gate circuit means receives the output of said first oscillator means as the continuous sine wave input signal thereof.

13. Velocity measurement apparatus according to claim 6, wherein said second means further includes second oscillator means for providing a continuous sine wave signal to said third gate circuit means.

14. Velocity measurement apparatus according to claim 13, wherein said second oscillator means has a frequency which is higher than said first oscillator means.

15. Velocity measurement apparatus according to claim 7, wherein said third gate circuit means receives the output of said first oscillator means as the continuous sine wave input signal thereof.

16. Velocity measurement apparatus according to claim 7, wherein said second means further includes second oscillator means for providing a continuous sine wave signal to said third gate circuit means.

17. Velocity measurement apparatus according to claim 16, wherein said second oscillator means has a frequency which is higher than said first oscillator means.

* * * * *